United States Patent
Dettmann et al.

(10) Patent No.: US 7,387,990 B2
(45) Date of Patent: Jun. 17, 2008

(54) ALKALINE DISINFECTING AND CLEANING COMPOSITIONS HAVING IMPROVED CLEANING EFFICIENCY

(75) Inventors: Andreas Dettmann, Hamburg (DE); Thomas Spuida, Norderstedt (DE)

(73) Assignee: Air Liquide Sante (International), Paris Cedex (FR)

( * ) Notice: Subject to any disclaimer, the term of this patent is extended or adjusted under 35 U.S.C. 154(b) by 0 days.

(21) Appl. No.: 11/704,296

(22) Filed: Feb. 9, 2007

(65) Prior Publication Data

US 2007/0197422 A1 Aug. 23, 2007

(30) Foreign Application Priority Data

Feb. 13, 2006 (DE) .................... 10 2006 006 765

(51) Int. Cl.
*C11D 1/835* (2006.01)
*C11D 1/62* (2006.01)
*C11D 3/30* (2006.01)

(52) U.S. Cl. ................ 510/384; 510/131; 510/161; 510/199; 510/218; 510/235; 510/237; 510/362; 510/382; 510/391; 510/421; 510/527; 510/499; 510/504

(58) Field of Classification Search ........... 510/131, 510/161, 199, 218, 235, 237, 362, 382, 384, 510/391, 421, 427, 504, 499
See application file for complete search history.

(56) References Cited

U.S. PATENT DOCUMENTS

| | | | |
|---|---|---|---|
| 3,936,538 A * | 2/1976 | Marshall et al. ............ | 510/519 |
| 5,576,284 A * | 11/1996 | van Buskirk et al. ....... | 510/384 |
| 5,856,290 A * | 1/1999 | van Buskirk et al. ....... | 510/382 |
| 6,303,557 B1 * | 10/2001 | Colclough .................. | 510/382 |
| 6,376,547 B1 * | 4/2002 | Behrends et al. ........... | 514/579 |
| 6,583,181 B1 * | 6/2003 | Chiang et al. .............. | 514/642 |
| 6,610,248 B1 * | 8/2003 | Lichtenberg et al. ......... | 422/28 |
| 6,939,840 B2 * | 9/2005 | Lichtenberg et al. ....... | 510/384 |
| 2006/0111265 A1 * | 5/2006 | Rypkema et al. ........... | 510/504 |
| 2006/0247150 A1 * | 11/2006 | Molinaro et al. ........... | 510/499 |

* cited by examiner

*Primary Examiner*—Charles I Boyer
(74) *Attorney, Agent, or Firm*—Young & Thompson

(57) ABSTRACT

The invention relates to an alkaline disinfecting and cleaning composition which comprises one or more selected quaternary ammonium salts, one or more selected alcohol alkoxylates and one or more alkylamines. By exact choice of the components a composition is provided which can be formulated as concentrate and, as dilute aqueous ready-to-use solution, has good cleaning efficiency combined with good microbicidal activity.

10 Claims, No Drawings

ALKALINE DISINFECTING AND CLEANING COMPOSITIONS HAVING IMPROVED CLEANING EFFICIENCY

The invention relates to alkaline disinfecting and cleaning compositions for hard surfaces, in particular for instruments and working surfaces in the food industry and in the hospital sector. The invention further relates to the use of the compositions for removing fatty soiling and for combating listerias and salmonellae.

Alkaline disinfecting and cleaning compositions for instruments and working surfaces in the food industry and in the hospital sector are known. For example, there is a commercial product based on benzalkonium chloride, phenoxypropanols and alkylamine which exhibits good microbiological activity, but only satisfactory cleaning capacity. However, a good alkaline disinfecting and cleaning composition must:

exhibit very good disinfecting activity and high cleaning efficiency and be readily able to be rinsed off,
remove even fatty soiling or residues and blood,
be bactericidally, fungicidally and virucidally active, in particular also against salmonellae and listerias,
be active even at low temperatures (e.g. about 10° C.) and in highly polluted areas, and
after use and after rinsing with water, it must leave behind no residue, or virtually no residue.

It was an object of the present invention to provide an alkaline composition which, as dilute ready-to-use solution, exhibits good cleaning activity and good disinfecting activity, can be formulated as a concentrate and which also, moreover, meets the abovementioned requirements.

It has now surprisingly been found that this object is achieved by an alkaline disinfecting and cleaning composition in the form of a concentrate which a) comprises 1 to 50% by weight of one or more quaternary ammonium salts of the formula $[R^1R^2R^3(CH_3)N]^+[X]^-$, where $R^1$ to $R^3$ can be identical or different and are selected from $C_1$- to $C_{30}$- alkyl, $C_1$- to $C_{30}$-alkenyl and mixed groups, which can have one or more atoms selected from O, S, N and P, b) 0.5 to 15% by weight of one or more $C_9$- to $C_{13}$-alcohol alkoxylates and c) 1 to 30% by weight of one or more alkylamines.

Quaternary Ammonium Salt

Quaternary ammonium salts used according to the invention are represented by the formula $[R^1R^2R^3(CH_3)N]+[X]^-$, where $R^1$ to $R^3$ can be identical or different and are selected from $C_1$- to $C_{30}$-alkyl, $C_1$- to $C_{30}$-alkenyl and mixed groups, which can have one or more atoms selected from O, S, N and P, where $R^1$ to $R^3$ are, for example, $C_8$- to $C_{14}$-alkyl or methyl, preferably $C_9$- to $C_{12}$-alkyl or methyl, such as $C_{10}$-alkyl or methyl. X is an anion (of an inorganic or organic acid). Not only the anion but also the cation of the quaternary ammonium salt can be polyvalent ions, which gives a stoichiometry $[A^{(n+)}]_m[K^{(m+)}]_n$.

Quaternary ammonium salts which are preferably used according to the invention are compounds of the formulae $[R^1N(CH_3)_3]+[X]^-$, $[R^1R^2N(CH_3)_2]+[X]^-$ and $[R^1R^2R^3(CH_3)N]+[X]^-$, where $R^1$ to $R^3$ independently of one another are selected from $C_8$- to $C_{14}$-alkyl and $-(CH_2-CHR^4O)_n-R^5$, where n is an integer from 1 to 20, preferably 1 to 5, and $R^4$ and $R^5$, which can be identical or different, are H and/or $C_1$- to $C_4$-alkyl, preferably H.

Suitable quaternary ammonium salts are, according to the invention, all quaternary ammonium salts of the abovementioned formula which are known in the prior art as are disclosed, for example, in WO 00/63337, which is incorporated here by reference. Preferably, however, dialkyldimethylammonium salts are used, for example dialkyldimethylammonium chlorides, the alkyl chains of which independently of one another are selected from $C_8$- to $C_{14}$-alkyl, preferably $C_9$- to $C_{12}$-alkyl, such as $C_{10}$- alkyl. In the dialkyldimethylammonium salts, one of the methyl groups can be an alkoxylated, for example ethoxylated, hydromethyl group, for example a dialkyl(poly(oxyethyl)methyl)methylammonium salt having 1 to 5 EO groups, the alkyl groups of which are decyl groups and in which propionate is present as anion, which is available from Lonza as Bardac® 26.

Exemplary anions and classes of anions of the inventively used quaternary ammonium salts are hydroxide, sulphate, hydrogen sulphate, methosulphate, ethosulphate, lauryl sulphate, lauryl ether sulphate, cellulose sulphate, sulphamate, halide (fluoride, chloride, bromide, iodide), nitrite, nitrate, carbonate, hydrogencarbonate, phosphate, alkyl phosphate, metaphosphate, polyphosphate, thiocyanate (rhodanide) carboxylic acid salt such as benzoate, lactate, acetate, propionate, citrate, succinate, glutarate, adipate, toluenesulphonate (tosylate) and salicylate. Particularly preferred anions are chloride and propionate.

Examples of preferred quaternary ammonium salts are the abovementioned didecylmethylpoly (oxyethyl) ammonium propionate (Bardac® 26) and didecyldimethylammonium chloride. A particularly preferred quaternary ammonium compound is didecyldimethylammonium chloride which is available from Lonza as an approximately 40% strength aqueous solution as BARDAC® 2240. Commercial products can also be used which comprise the quaternary ammonium compound dissolved in a small amount of alcohol, such as BARDAC® 22 having about 50% by weight of didecyldimethylammonium chloride and 19.5 to 24.5% by weight of isopropanol in aqueous solution.

In a preferred embodiment, the inventive composition comprises in the form of a concentrate 2 to 30% by weight, preferably 5 to 25% by weight, in particular 7.5 to 15% by weight, for instance approximately 10% by weight, of the quaternary ammonium salt (or of the two, three, four, etc. quaternary ammonium salts). The amount of quaternary ammonium salt here is recorded according to the invention as quaternary ammonium chloride.

Preferred compositions are free from benzalkonium compound (such as benzalkonium chloride). In a preferred embodiment, the invention relates to an alkaline disinfecting and cleaning composition which, as quaternary ammonium salt, comprises dialkyldimethylammniumo salt (such as dialkyldimethylammonium chloride, in particular didecyldimethylammonium chloride) and which is free from benzalkonium chloride. Preference is also given to compositions which, in addition to didecyldimethylammonium chloride, comprise no further quaternary ammonium salt.

It has surprisingly been found that benzalkonium chloride, in the system quaternary ammonium compound/alkylamine, is significantly weaker with respect to the cleaning efficiency towards fatty dirt than the quaternary ammonium salts used according to the invention, correspondingly, the required amount of quaternary ammonium compound which is necessary to remove fatty dirt, is less when the composition is free from benzalkonium compound (in particular benzalkonium chloride) and, as quaternary ammonium compound, only comprises the abovementioned quaternary ammonium salts.

$C_9$- to $C_{13}$-alcohol Alkoxylate

The inventively used $C_9$- to $C_{13}$-alcohol alkoxylates (alkylalcohol alkoxylates) are nonionic surfactants and ensure that the mixture of quaternary ammonium salt with alkylamine as concentrate is a homogeneous, liquid and clear mixture and, in addition, the ready-to-use solutions are stabilized. Preferred alcohol alkoxylates are alcohol ethoxylates having 5 to 13 EO units, preferably $C_{10}$- to $C_{13}$-alcohol ethoxylates having 5 to 12 EO units, such as 7 to 12 EO units. Particular preference is given to isotridecanol-12EO (e.g. Marlipal® 013/120).

Generally, good cleaning efficiency is known of alcohol alkoxylates as nonionic surfactants. It was therefore surprising that the cleaning efficiency in the system quat/alkylamine is inhibited by a comparatively high amount of alcohol alkoxylate, as is shown in the examples.

The selection of an inventive concentration range ensures disinfecting activity and cleaning efficiency, and also concentrate stability and stability of the ready-to-use solution (homogeneity, clarity). The alcohol alkoxylate is used in the concentrate, preferably in an amount of 0.75 to 10% by weight, more preferably 1 to 8% by weight, in particular 1.5 to 5% by weight, for instance 2.5% by weight. In a preferred embodiment, the amount of alcohol alkoxylate in the concentrate is restricted, however, to <7.5% by weight, preferably <6% by weight, more preferably <5% by weight.

Alkylamine

The inventive composition comprises one or more alkylamines. A particularly preferred amine is N,N-bis(3-aminopropyl)dodecylamine (Lonzabac 12.100). In addition, alkylpropylenediamine (Genamin LAP 100 D®) is suitable.

Inventive compositions are present as concentrate with a pH from 8.5 to 9.2. In the ready-to-use solutions, the pHs are from 8.0 to 8.7, depending on initial concentration (0.25 to 2% by volume), measured in water of standardized hardness as specified in the EURO standard.

The inventive composition is preferably aldehyde-free, free from phenol and/or phenol derivatives and/or free from active oxygen compounds such as hydrogen peroxide. Inventive compositions can, in addition, comprise one or more functional additives, for example buffers, cleaning boosters, solvents, hydrotropes, corrosion inhibitors, complexing agents, odour absorbers, stabilizers, foam inhibitors, care components, pH correctors, perfumes and dyes. An inventive composition, however, need not be formulated with perfume and/or dye and is therefore preferably free from perfume and/or dye.

A particularly preferred composition in the form of a concentrate is characterized in that it
a) comprises 10 to 20% by weight of dialkyldimethylammonium salt, such as didecyldimethylammonium dichloride,
b) 1.5 to 5% by weight of $C_{10}$- to $C_{13}$-isoalkylalcohol ethoxylate having 7 to 12 EO units,
c) 1 to 30% by weight of alkylamine.

The invention further relates to an alkaline disinfecting and cleaning composition in the form of an aqueous ready-to-use solution which comprises 0.1 to 10% by volume, preferably 0.25 to 5% by volume, for instance 2.5% by volume, of the abovementioned concentrate.

The invention further relates to the use of the concentrate or of the aqueous ready-to-use solution for removing fatty soiling and blood, in particular from instruments and working surfaces in the food industry and in the hospital sector. In addition, the invention relates to the use of the concentrate or of the aqueous ready-to-use solution for combating bacteria and fungi, in particular salmonellae and listerias.

The inventive concentrates have the following advantages:

The concentrates have a comparatively low content of quaternary ammonium compound as active ingredient compared with benzalkonium chloride-containing compositions which comprise additional active ingredients. Therefore, the total active ingredient content of the (dilute) aqueous ready-to-use solution is lower for the same initial concentration of the concentrate, which results in cost and environmental advantages, while the bactericidal and fungicidal activity of the inventive concentration is retained.

Their bactericidal and fungicidal activity is, for the same initial concentration of the concentrate in a ready-to-use solution, not impaired compared with previously known concentrates comprising benzalkonium chloride.

They can be formulated using a comparatively low amount of nonionic surfactant (alcohol alkoxylate) to form clear solutions, while simultaneously, excellent cleaning efficiency is still achieved using the aqueous ready-to-use solution.

They exhibit good storage stability.

These advantages are also achieved in the dilute aqueous ready-to-use solution.

EXAMPLES

Percentages, unless stated otherwise, are in % by weight.

Method A Determination of Cleaning Activity Using Different Test Fouling

The method serves for determining the static and dynamic cleaning efficiency of solutions towards various types of test fouling. The method is especially suitable for evaluating the cleaning efficiency of cleaners and disinfecting compositions. A microscope slide furnished with the fouling is then held for a certain time in the optionally stirred solution.

1. Test Fouling:

1.1 Beef Blood:

Defibrinated beef blood obtainable from Fiebig-Nährstoff-technik. Amount about 10 mg per microscope slide.

1.2 Beef Tallow:

50 g of beef tallow are stained with 0.5 g of Fettrot, the beef tallow is melted before application. Amount about 25 mg per microscope slide.

1.3 Lard:

50 g of lard are stained with 0.02 g of Fettrot. The lard is melted before application. Amount about 50 mg per microscope slide.

1.4 Egg Yolk (on the Basis of DIN 44990, Part 2):

To provide 100 ml of egg yolk test fouling, about 15 eggs are warmed for 30 minutes in warm water at 20° C., and placed in boiling water for 4.5 minutes, then cooled for 5 minutes in warm water at 20° C., opened, and the still-liquid egg yolk is removed. The egg yolk is stored in the refrigerator in a screw-top glass. Amount about 50 mg per microscope slide.

1.5 Semolina Paste:

To prepare 100 ml of semolina paste test fouling, 10 g of skimmed milk powder, 5 g of sugar, 4 g of butter and 4 g of hard wheat semolina are required. The skimmed milk powder is stirred into 100 ml of tap water. After dissolution of the milk powder, the sugar and the butter are added and the mixture is brought to boiling in the water bath. The semolina is stirred into the boiling liquid and heated with occasional stirring for 20 minutes in the boiling water bath. The semolina paste test fouling is stored in the refrigerator in a screw-top glass. Amount about 20 mg per microscope slide.

2. Procedure:

Glass microscope slides (76×26 mm) are labelled by engraving or using a pencil for later identification. The microscope slides are successively washed with acetone, petroleum ether and petroleum ether again, and thereafter weighed.

The cleaned microscope slides are placed next to one another on a tray covered with a cellulose cloth. A 10 mm wide bristle brush is dipped into the test fouling and lightly wiped off on the vessel rim. A uniform test fouling layer is then applied with a rapid motion from top to bottom. A rim of at least 5 mm should remain free on all sides. After an initial drying time of about 1 hour at room temperature, the microscope slides are placed in a storage box. The open box is kept overnight in the desiccator over silica gel for complete drying of the sample bodies. Thereafter the microscope slides with the dried test fouling layer are weighed once more.

2.1 Static Cleaning Test

Glass beakers (100 ml, high type) are carefully filled with about 100 ml of the test solution, during which the surface of the solution should remain foam-free. The microscope slides are carefully placed into the solution using tweezers, with the test fouling layer upwards. After the end of the test time, the microscope slides are carefully removed from the solution by the tweezers and rinsed in demineralized water by careful immersion and tilting. The microscope slides are then dried in air vertically upright and, after drying for about 1 hour, are placed in the storage box. The open storage box is kept overnight in the desiccator over silica gel for further drying. Thereafter, the third weighing follows. It is advisable to perform duplicate determination.

2.2 Dynamic Cleaning Test

Glass beakers (250 ml, high type) are filled with about 200 ml of the test solution, provided with a magnetic stirrer bar (diameter 30 mm) and positioned on a magnetic stirrer so that the course of stirring is centred. The microscope slides, held by a test tube chamber, are immersed in the solution. The magnetic stirrer is then started (about 430 rpm). After the end of the test time, the microscope slides are removed from the solution and rinsed in demineralized water by careful immersion and tilting. The microscope slides are then dried in air vertically upright and, after drying for 1 hour, are placed in the storage box. For further drying, the open storage box is kept overnight in the desiccator over silica gel. Thereafter the third weighing follows. It is advisable to carry out a duplicate determination.

The cleaning efficiency is evaluated by reporting the percentage by weight of test fouling removed. The type of test fouling, test time and test temperature must be reported.

Method B

Fungicidal and Bactericidal Activity of the Compositions

The fungicidal and bactericidal activity was tested as specified by DIN EN 1650 (1997), DIN EN 1276 (1997) and DIN EN 13697 (2001).

Method C

Activity Against *Listeria Monocytogenes*

The bactericidal activity with protein load was tested on the basis of the "Richtlinien für die Prüfung chemischer Desinfektionsmittel (Methoden zur Prüfung von Desinfektionsmitteln gegen Bakterien und Pilze in Bereichen des Herstellens, Inverkehrbringens und Behandelns von Tieren stammender Lebensmittel)" [Guidelines for testing chemical disinfecting compositions (Methods for testing disinfecting compositions against bacteria and fungi in the fields of production, putting into commerce and treating foods of animal origin] of the Deutsche Veterinärmedizinische Gesellschaft, 3rd edition, 2000. The test microorganism used was ATCC 35152, and nutrient media used were (1) casein-soyabean meal peptone-agar+1% glucose+1% defibrinated sheep's blood, (2) Brain-Heart-Infusion (difco 237400) and (3) Brain-Heart-Infusion Columbia-blood-agar (Bd 4007708). To dilute the test preparation for the control test, use was made of water of standardized hardness which had been boiled briefly before each use. All tests were carried out at 20 ±1° C. The protein load was achieved by 10% sterile beef serum inactivated at 65° C. in 30 minutes, from UNIPATH GmbH, Wesel. The bactericidal activity was determined in a quantitative suspension test in 10% beef serum as organic load. The inactivation medium used was 3% Tween 80 + 3.0% saponin +0.1% histidine +0.1% cysteine in Brain-Heart-Infusion (TSHC).

Method D

Activity Against *Salmonella Choleraesuis*

The test was performed as specified in DIN EN 1276 (1997) (ATCC 43974).

Formulations Used

|  | I | II (comparison) | III (comparison) | IV (comparison) |
|---|---|---|---|---|
| Benzalkonium chloride |  | 10 |  | 10 |
| Didecyldimethyl-ammonium chloride | 10 |  | 10 |  |
| $C_{13}$-alcohol-12EO | 2.5 | 2.5 | 20 | 5 |
| Malic acid (pH regulator) | 0.5 | 0.5 | 0.5 |  |
| Lonzabac 12.100 | 2 | 2 | 2 | 3 |
| Citric acid monohydrate |  |  |  | 1 |
| Phenoxypropanol |  |  |  | 1.5 |
| Plurafac LF 231 |  |  |  | 3 |
| Demineralized water | ad 100 g | ad 100 g | ad 100 g | ad 100 g |

Example 1

Cleaning Efficiency

In a cleaning test under the following conditions:
test fouling: beef tallow,
method: dynamic cleaning test at room temperature,
2% by volume of the concentrate in water the following results were obtained:

| | |
|---|---|
| Composition I | 100% |
| Composition II | 1% |
| Composition III | 78% |
| Composition IV | 6% |

These results verify the advantageous cleaning efficiency with the use of inventive concentrates whose constituents are exactly matched to one another. While the inventive concentrate I exhibits a very good cleaning efficiency, the cleaning capacity with the use of comparison concentrates II, III and IV is markedly poorer.

Example 2

Bactericidal and Fungicidal Activity of Concentrate I 2.1 Activity Against *Listeria Monocytogenes* (Method C):
The inventive concentrate I is fully active against *Listeria monocytogenes* (ATCC 35152) (reduction in microbial count by more than 4 powers of ten) at a test temperature of 20° C. as 0.25% by volume ready-to-use solution for an exposure time of 5 minutes.

2.2 Activity Against *Salmonella Choleraesuis* (Method D):
The inventive concentrate I, as 0.5% by volume solution in a dilution, after 15 minutes with a protein load, has sufficient bactericidal activity against the bacterial strain *Salmonella choleraesuis* ATCC 43947.

2.3 Fungicidal and Bactericidal Activity
High load =3.0 g/l of beef albumin,
Low load =0.3 g/l of beef albumin,
Fungicidal activity =activity against *C. albicans* and *A. niger*,
Bactericidal activity =activity against *P. aeruginosa, E. coli, S. aureus* and *E. hirae*.

| Test | Result |
|---|---|
| EN 1276 (1997), low load, 20° C. 0.25% by volume | Activity in 5 min |
| EN 1276 (1997), low load, 10° C. 0.5% by volume | Activity in 5 min |
| EN 1276 (1997), high load, 20° C. 0.5% by volume | Activity in 5 min |
| EN 1276 (1997), high load, 10° C. 0.5% by volume | Activity in 5 min |
| EN 1650 (1997), low load, 20° C. 0.25% by volume | Activity in 30 min |
| EN 1650 (1997), low load, 10° C. 0.5% by volume | Activity in 30 min |
| EN 1650 (1997), high load, 20° C. 0.5% by volume | Activity in 60 min |
| EN 1650 (1997), high load, 10° C. 1% by volume | Activity in 60 min |
| EN 13697 (2001), low load, 20° C. 0.25% by volume | Bactericidal activity in 30 min |
| EN 13697 (2001), low load, 10° C. 0.5% by volume | Bactericidal activity in 60 min |
| EN 13697 (2001), high load, 20° C. 0.5% by volume | Bactericidal activity in 30 min |
| EN 13697 (2001), high load, 10° C. 1% by volume | Bactericidal activity in 60 min |
| EN 13697 (2001), low load, 20° C. 0.25% by volume | Fungicidal activity in 30 min |
| EN 13697 (2001), low load, 10° C. 0.5% by volume | Fungicidal activity in 60 min |
| EN 13697 (2001), high load, 20° C. 0.5% by volume | Fungicidal activity in 60 min |
| EN 13697 (2001), high load, 10° C. 2% by volume | Fungicidal activity in 60 min |

The invention claimed is:

1. An alkaline disinfecting and cleaning composition in the form of a concentrate, comprising
   a) 7.5 to 15% by weight of dialkyldimethylammonium salt;
   b) 1.5 to 5% by weight of $C_{10}$- to $C_{13}$-isoalkylalcohol ethoxylate having 7 to 12 EO units; and
   c) 1 to 15% by weight of N,N-bis(3-aminopropyl)-dodecylamine.

2. The concentrate according to claim 1, characterized in that it is free from aldehyde, phenol or phenol derivative and/or active oxygen compound.

3. The concentrate according to claim 1, characterized in that it is free from a benzalkonium compound.

4. The concentrate according to claim 1, characterized in that said dialkyldimethyl-ammonium salt is didecyldimethyl ammonium dichloride.

5. The concentrate according to claim 1, characterized in that it is free from perfume and/or dye.

6. The concentrate according to claim 1, characterized in that it comprises didecyldimethylammonium chloride as sole quaternary ammonium compound.

7. The concentrate according to claim 1, characterized in that in addition it comprises one or more functional additives selected from the group consisting of perfumes, dyes, buffers, cleaning boosters, solvents, hydrotropes, corrosion inhibitors, complexing agents, odour absorbers, stabilizers, foam inhibitors, care components and pH correctors.

8. An alkaline disinfecting and cleaning composition in the form of an aqueous ready-to-use solution, comprising 0.1 to 10% by volume, preferably 0.25 to 5% by volume, for instance 2% by volume, of the concentrate according to claim 1.

9. A method of removing fatty soiling and blood from a hard surface, which comprises applying an effective amount of the concentrate according to claim 1, to said surface.

10. A method of combating bacteria and fungi, in particular salmonellae and listerias from a hard surface, which comprises adding an effective amount of the aqueous ready-to-use solution according to claim 8 to said surface.

* * * * *